US007552494B2

(12) United States Patent
Peterson

(10) Patent No.: US 7,552,494 B2
(45) Date of Patent: Jun. 30, 2009

(54) METHOD AND APPARATUS FOR MANUFACTURING CUSTOM ORTHOTIC FOOTBEDS THAT ACCOMMODATE THE EFFECTS OF TIBIAL TORSION

(75) Inventor: William E. Peterson, Newport, RI (US)

(73) Assignee: eSoles, L.L.C., Scottsdale, AZ (US)

( * ) Notice: Subject to any disclaimer, the term of this patent is extended or adjusted under 35 U.S.C. 154(b) by 878 days.

(21) Appl. No.: 11/160,025

(22) Filed: Jun. 6, 2005

(65) Prior Publication Data

US 2006/0247892 A1 Nov. 2, 2006

Related U.S. Application Data

(63) Continuation-in-part of application No. 11/116,738, filed on Apr. 28, 2005, now Pat. No. 7,392,559.

(51) Int. Cl.
    *A43D 11/00* (2006.01)
(52) U.S. Cl. .......................... 12/1 R; 12/142 R; 33/3 R
(58) Field of Classification Search ................ 12/1 R, 12/142 R, 142 N; 33/3 R, 6, 3 B, 3 C
See application file for complete search history.

(56) References Cited

U.S. PATENT DOCUMENTS

| 4,745,290 A | 5/1988 | Frankel et al. |
| 5,054,148 A | 10/1991 | Grumbine |
| 5,206,804 A | 4/1993 | Thies et al. |
| 5,237,520 A | 8/1993 | White |
| 5,282,328 A | 2/1994 | Peterson |
| 5,339,252 A | 8/1994 | White et al. |
| 5,477,371 A | 12/1995 | Shafir |
| 5,659,395 A | 8/1997 | Brown et al. |
| 5,671,055 A | 9/1997 | Whittlesey et al. |
| 5,689,446 A * | 11/1997 | Sundman et al. ............. 702/167 |
| 5,790,256 A | 8/1998 | Brown et al. |
| 6,006,412 A | 12/1999 | Bergmann et al. |

(Continued)

FOREIGN PATENT DOCUMENTS

EP 0829209 A1 3/1998

(Continued)

OTHER PUBLICATIONS

International Search Report for PCT/US2006/016,116 dated Sep. 28, 2006.
Written Opinion of the International Searching Authority for PCT/US2006/016,116 dated Sep. 28, 2006.

*Primary Examiner*—Marie Patterson
(74) *Attorney, Agent, or Firm*—George A. Herbster

(57) ABSTRACT

A method and apparatus for providing a topographical map of the bottom of a patient's rear foot with the foot in a semi-weight bearing condition and in the neutral position adjusted for the effects of tibial torsion. A foot scanner with a pivoted air cushion is adjusted to a first position whereupon the foot is captured. Then the air cushion is oscillated relative to the first position until the talus and navicular exhibit congruency to establish a measurement position. A three-dimensional scanner measures the distances corresponding to the spacing between a reference plane and the bottom of at least the rear foot and midfoot. A manufacturing facility converts these measurements into information by which computer numerical controlled equipment machines an orthotic insert for the patient's footwear.

36 Claims, 15 Drawing Sheets

U.S. PATENT DOCUMENTS

| | | |
|---|---|---|
| 6,042,759 A | 3/2000 | Marshall |
| 6,141,889 A | 11/2000 | Baum |
| 6,205,230 B1 | 3/2001 | Sundman et al. |
| 6,463,351 B1 | 10/2002 | Clynch |
| 6,523,206 B2 | 2/2003 | Royall |
| 6,654,705 B1 | 11/2003 | Benson et al. |
| 6,692,454 B1 | 2/2004 | Townsend et al. |
| 6,741,728 B1 | 5/2004 | Genest |
| 6,909,513 B1 * | 6/2005 | Fujita et al. ............... 356/601 |
| 7,068,379 B2 | 6/2006 | Sundman |
| 7,392,559 B2 * | 7/2008 | Peterson ..................... 12/1 R |
| 2001/0002232 A1 | 5/2001 | Young et al. |
| 2002/0138923 A1 | 10/2002 | Shaffeeullah |
| 2003/0009354 A1 | 1/2003 | Arbogast et al. |
| 2004/0133431 A1 | 7/2004 | Udiljak et al. |
| 2004/0168329 A1 | 9/2004 | Ishimaru |
| 2006/0103852 A1 | 5/2006 | Klaveness |

FOREIGN PATENT DOCUMENTS

| | | |
|---|---|---|
| EP | 00990398 A2 | 5/2000 |
| GB | 434733 | 9/1935 |
| JP | 2004219404 | 8/2004 |
| WO | 98/18386 | 5/1998 |
| WO | WO 02/34157 A2 | 5/2002 |
| WO | WO03/087717 | 10/2003 |

* cited by examiner

METHOD AND APPARATUS FOR MANUFACTURING CUSTOM ORTHOTIC FOOTBEDS THAT ACCOMMODATE THE EFFECTS OF TIBIAL TORSION

CROSS REFERENCE TO RELATED APPLICATION

This application is a continuation-in-part of co-pending U.S. patent application Ser. No. 11/116,738 filed Apr. 28, 2005 for a Method and Apparatus for Manufacturing Custom Orthotic Footbeds.

FIELD OF THE INVENTION

This invention generally relates to foot orthotics. More specifically this invention relates to a methodology and apparatus for producing custom orthotic footbeds that accommodate the effects of tibial torsion and that are acceptable for therapeutic applications as defined by medical personnel.

DESCRIPTION OF RELATED ART

An individual should stand with each of his or her feet in an optimal anatomical position called a "referenced neutral position." However, in most individuals the foot naturally assumes a position that is different from that referenced neutral position. Orthotic footbeds are inserted into footwear, such as a shoe, to reposition the foot to that referenced neutral position or as close to that position as the individual can tolerate.

Many methods exist for producing orthotic footbeds that support a foot in the referenced neutral position. The gold standard and dominant methodology used by medical personnel for producing orthotic footbeds involves forming a plaster cast and mold. In accordance with this process, a practitioner produces a plaster cast of each of a patient's feet after manipulating each foot to the referenced neutral position subject to compensation for any observed anatomical deformities of that foot. The non-weight bearing condition exists when no forces are applied to the foot, as when the foot is suspended in air.

The practitioner sends these casts to a laboratory where laboratory personnel make a mold from the cast and then use the patient information, a priori knowledge of the practitioner's procedures and other experience to modify the patient's molds. Next personnel at the laboratory use each mold to form a corresponding orthotic block which is finished at the laboratory and returned to the practitioner as an orthotic footbed.

The practitioner then dispenses the orthotic footbed to the patient. If a patient reports only little or no relief or reports discomfort, the practitioner must reevaluate the patient. If changes to the orthotic footbed are required, then either the entire process must be repeated or the orthotic footbed must be sent back to the laboratory with instructions for additional corrections.

Other methodologies have been proposed. For example, my U.S. Pat. No. 5,282,328 discloses a pillow set of left-foot and right-foot composite foam pillows for positioning feet toward the referenced neutral foot position. These pillow sets do facilitate the production of custom footbeds. However, each pillow set is based upon averages for people in a design weight range. Consequently although the footbed is adequate and provides improvements for many applications, these pillows can introduce minor errors or deviations from the optimum for that individual.

Footbeds are produced on these pillows with the feet in either a full weight-bearing condition or a semi-weight-bearing condition. A semi-weight-bearing condition exists when a patient sits so only the weight of the leg produces forces on the bottom of the foot. A full weight-bearing condition exists when the patient stands so the feet support the entirety of the patient's weight. Footbeds made with the feet in a full weight-bearing condition are particularly adapted for insertion in ski boots or other footwear when the individual's feet will be subjected to various dynamic forces. However, it can be difficult to achieve complete anatomical alignment when these composite foam blocks are used in the full weight-bearing condition. When the composite foam blocks are used in a semi-weight bearing mode, it is easier to achieve such an anatomical alignment and to compensate for certain deformities. However, it can be challenging to position the feet properly to achieve this result, so the process tends to be time consuming.

U.S. Pat. No. 6,141,889 to Baum discloses a custom foot support and method for producing such a foot support based upon a scan of the foot. According to the disclosure, an optical scanner captures a three-dimensional image of the bottom of the foot in a non-weight bearing, semi-weight bearing or full weight bearing condition. The captured images from this scanner are then exported to a central system for use in the production of a footbed. Data relating to the patient's sex, weight, age, foot type and shoe style serve to modify the captured images. Some of this data is taken from tables based upon averages. So it is unlikely that a modification based upon an average will produce the exact modification the patient requires. Consequently such foot supports may achieve only some of the objectives that would be achieved by the gold standard approach.

U.S. Pat. No. 6,654,705 to Benson et al. is an example of a system for detecting a surface contour of the human foot with an array of biased, vertically displaceable sensing pins. In these systems an individual stands on a support plate. The pins extend through the plate until they contact the bottom of the foot to provide an array of measurements. In the Benson et al. patent, a person places a foot on an upper support plate that deflects downwardly until the pins pass through the plate and contact a portion of the foot. As each pin contacts the foot, further downward displacement displaces the pin. A counter records decrements of vertical movement for each pin. A final count, when the system is in equilibrium, corresponds to the relative vertical displacement of a corresponding foot position in relation to a reference plane. In other embodiments, the pins are driven upward through the support plate pneumatically until they contact the bottom of the foot. Then the system is "locked" to obtain measurements of the deflection of each pin.

In both embodiments of the Benson et al. patent the final information for all the pins provides a digital representation of the sensed contour or topography of the foot. This digital data provides a contour image of the foot and medical information concerning the shape of the foot. As the measurements are made in the full weight-bearing condition, the foot tends to be elongated and the arch tends to flatten. Further, the spatial resolution of the measurements does not provide an accurate representation of the bottom of the foot for medically acceptable orthotics.

U.S. Patent Application Publication No. 2001/0002232 to Young et al. discloses a method and system for forming custom shoe insoles or footbeds by positioning a foot at a scanning station. The scanning station includes at least one laser unit which scans an undersurface of the foot in a full weight-bearing condition on a flat transparent plate. The measured surface coordinates are processed and transmitted to a computer. As the foot is scanned in the full weight-bearing condition, the arch is flattened and the foot is elongated. Moreover, there is no guarantee that the resulting insoles will support the patient's feet in the referenced neutral position and accommodate any anatomical deformation.

Each of the foregoing and other alternatives for providing measurements without the use of casts and molds can reduce the labor involved and provide the information without the need for the problems of producing casts and the like. However, practitioners who prescribe orthotic footbeds, particularly for medical reasons, continue to use the gold standard by making plaster casts and molds despite the disadvantages and complexities of that process.

Some of these methodologies do address certain anatomical deformities. For example, U.S. patent application Ser. No. 11/116,738 addresses anatomical deformities that give rise to conditions of the foot known as varus and valgus. However, none of these references address the effects of tibial torsion. Tibial torsion is a twisting of the shin bone resulting from prenatal conditions or hereditary or both. Internal tibial torsion twists the foot inward at the toes so that the feet assume a condition commonly known as being pigeon toed. External tibial torsion twists the feet outward. As described later, if an orthotic footbed does not accommodate the effects of tibial torsion, the individual's feet may be constantly pronated or supinated thereby adversely affecting the value of the orthotic footbed.

What is needed is an apparatus and method for producing medically acceptable orthotic footbeds that have the quality of the prior art gold standard but that account for the effects of tibial torsion. What is also needed is a method and apparatus that facilitates the measurement of the bottom of the foot in a referenced neutral position thereby to provide information for the automated manufacture of orthotics that correct for various problems a patient may have with his or her feet including the effects of tibial torsion.

SUMMARY

Therefore it is an object of this invention to provide a method and apparatus for facilitating the generation of information useful in producing medically acceptable orthotic footbeds for insertion in an individual's footwear.

Another object of this invention is to provide a method and apparatus for facilitating the generation of information about the contour of an individual's foot in a referenced neutral position taking tibial torsion into account.

Still another object of this invention is to enable the production of a medically acceptable orthotic footbed that takes the effects of tibial torsion into account while eliminating the need for the practitioner to produce a cast and for laboratory personnel to make a mold.

In accordance with this invention, a custom orthotic footbed for a patient's footwear is based upon a representation of the topography of the bottom of the patient's foot relative to a transverse reference plane extending along a foot axis. A measurement of the effective tibial torsion is obtained by determining an angle of the patient's lower leg and foot due to tibial torsion. The foot measurement device is then rotated to a first position by displacing the foot axis from the frontal axis by an angle corresponding to the patient's tibial torsion angle. The foot is captured in the foot measurement device in this first position. Next the foot measurement device is manipulated transversely proximate the first position until the patient's talus and navicular exhibit congruency thereby to establish a measurement position. The topographical record of the foot with the measurement device is obtained in this measurement position.

A foot scanning apparatus for obtaining a representation of the bottom of a patient's foot constructed for use in the production of custom orthotic footbed in accordance with another aspect of this invention generates a representation of the topography of the bottom of the foot. A framework positions the foot scanning apparatus on a support surface. A pivoted mount supports the foot measurement device on the framework whereby the foot measurement device is enabled to pivot through a limited angular range with respect to a reference position.

BRIEF DESCRIPTION OF THE DRAWINGS

The appended claims particularly point out and distinctly claim the subject matter of this invention. The various objects, advantages and novel features of this invention will be more fully apparent from a reading of the following detailed description in conjunction with the accompanying drawings in which like reference numerals refer to like parts, and in which:

DESCRIPTION OF ILLUSTRATIVE EMBODIMENTS

Figure 1:
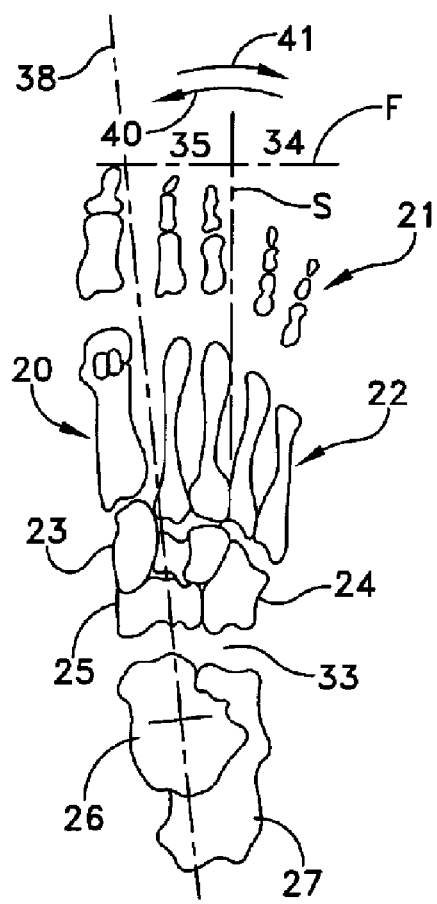
FIG. 1 is a transverse view of an individual's right foot.
Figure 2:
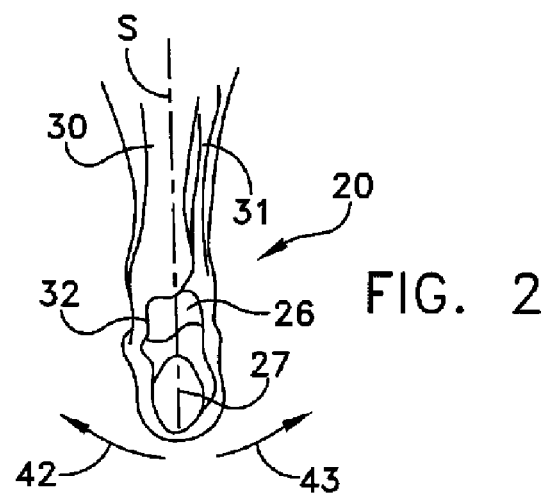
FIG. 2 is a view of the foot of FIG. 1 in the frontal plane, but viewed from the rear.
Figure 3:
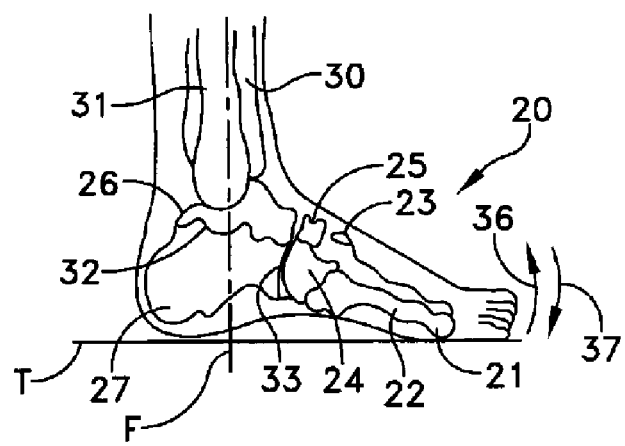
FIG. 3 is a view of the foot of FIG. 1 in a sagittal plane viewed from the right.

Before discussing a specific embodiment of this invention, it will be helpful to discuss the known anatomy of a foot as show in FIGS. 1 through 3 that depict the various bones and joints in a right foot and lower leg 20.

Lower Leg and Foot Anatomy

Referring to FIG. 1 the phalanges 21 form the toes. They are collectively the "forefoot" in this disclosure, and they connect to the "midfoot" that includes metatarsals 22, cuneiforms 23, the cuboid 24 and navicular 25. The "rear foot" includes talus 26 and the calcaneus 27. The calcaneus 27 interconnects the foot to the tibia 30 and the fibula 31. A subtalar joint 32 constitutes the interface between the talus 26 and the calcaneus 27. A midtarsal joint 33 comprises the interface between the cuboid 24, navicular 25, talus 26 and the calcaneus 27.

The foot is divided into two columns. As shown in FIG. 1 a lateral or lateral load-bearing column 34 comprise the calcaneus 27, the cuboid 24 and the fourth and fifth ray of the phalanges 21 and metatarsals 22. This represents the outer portion of the foot including the fourth and fifth toes. A medial or medial dynamic column 35 comprises the talus 26, the navicular 25, the cuneiforms 23 and rays one, two and three of the metatarsals 22 and phalanges 21. This corresponds to the inner section of the foot including the first three toes or digits.

Component motions in single planes often define complex motions and include dorsiflexion and plantar flexion in a sagittal plane S, adduction and abduction in a transverse plane T, and inversion and eversion in a frontal plane F. As shown in FIG. 3 the foot undergoes dorsiflexion when the distal end of the foot elevates toward the leg as represented by arrow 36 about a sagittal axis; plantar flexion is the reverse motion as represented by arrow 37. In the following discussion, the phrase "alignment axis 38" represents an axis that extends through a center of the talus 26 past a position between the first and second phalanges. Adduction is motion about a vertical or transverse axis toward the midline of the body represented by arrow 40 in FIG. 1; abduction is motion away from the midline of the body as represented by arrow 41. As shown in FIG. 2, inversion is movement of the foot about a frontal axis toward the midline of the body represented by arrow 42 whereas eversion is movement of the foot away from the midline of the body as represented by arrow 43.

Complex motions called "pronation" and "supination" include motions with respect to the ankle, subtalar and midtarsal joints. Pronation includes dorsiflexion, abduction and eversion; supination includes plantar flexion, adduction and inversion. During pronation, dorsiflexion is prominent at the ankle joint, eversion at the subtalar joint and abduction at the forefoot or phalanges 21; during supination, plantar flexion is prominent at the ankle joint, inversion at the subtalar joint and adduction at the forefoot.

In general terms, the optimal anatomical position for a rear foot is a "referenced neutral position" that exists when the subtalar joint 32 is in its neutral position and the forefoot has been locked against the rear foot. The subtalar joint neutral position is defined as the position of the subtalar joint 32 where the joint is congruent (i.e., the talus 26 and calcaneus 27 are on top of one another and the talus 26 and navicular 25 are congruent) and a bi-section of the lower one-third of the leg creates an angle with a bi-section of the posterior portion of the calcaneus 27. Ideally this occurs when the angle is about 3° to 4° varus (i.e., a fixed position of eversion) with the bi-section of the posterior portion of the calcaneus. The forefoot is locked against the rear foot by applying an upward force against the fourth and fifth metatarsal heads.

Figure 4A:
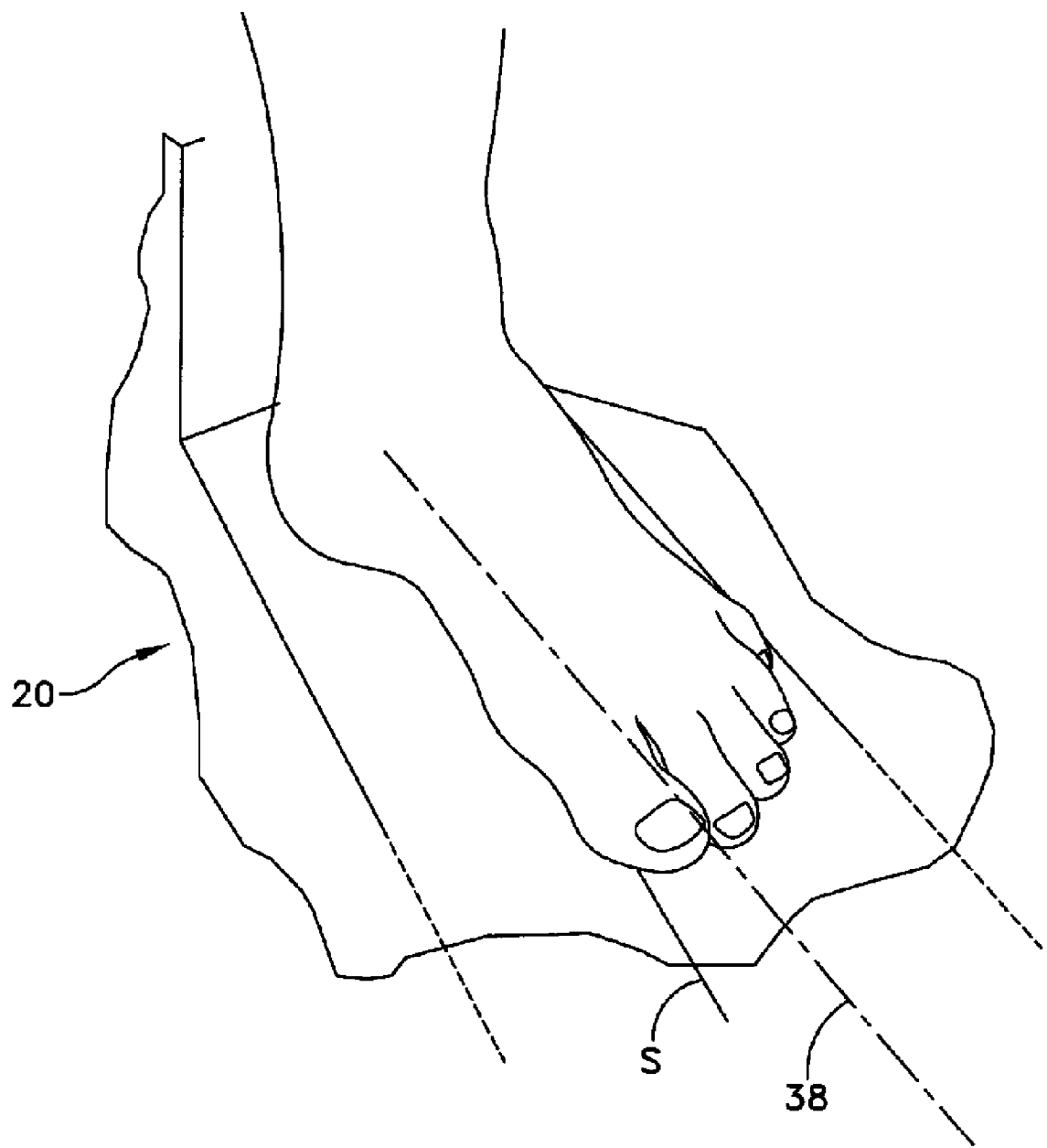
FIGS. 4A and 4B depict perspective views of a right foot for the purposes of explaining the effects of tibial torsion.
Figure 4B:
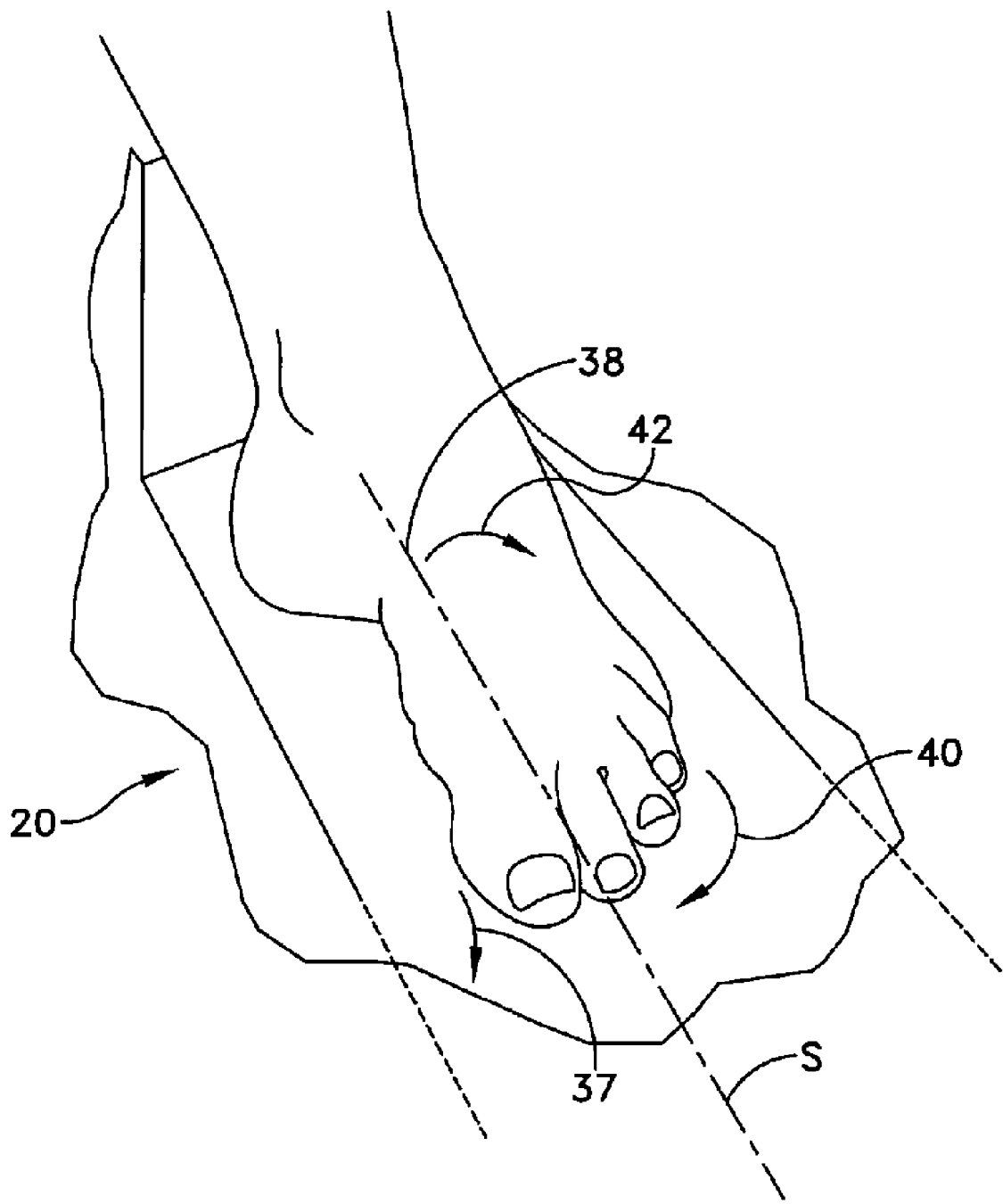

FIGS. 4A and 4B show the effects of external tibial torsion. More specifically in FIG. 4A the alignment axis 38 that shows the twisting of the lower leg and foot 20 about a vertical or transverse axis due to external tibial torsion. If this condition exists and the foot is rotated so an alignment axis lies in a sagittal plane S as shown in FIG. 4B, the foot 20 supinates. More specifically, the foot 20 supinates as characterized by inversion shown by arrow 42, adduction shown by arrow 40 and plantar flexion as shown by arrow 37. If the lower leg and foot 20 exhibited the effects of internal tibial torsion, moving the foot 20 so the alignment axis 38 lies in a sagittal plane would pronate the foot.

Prior art scanners, and even the scanner disclosed in U.S. patent application Ser. No. 11/116,738, operates so that the alignment axis 38 lies in a sagittal plane. If the amount of tibial torsion a patient exhibits is minimal, the impact of the resulting supination or pronation produced by the orthotic footbed is minimal and in many cases has no impact on the patient's anatomy.

However, as the amount of tibial torsion increases, the amount of corresponding supination or pronation can have an adverse impact on the support provided by the custom footbed. More specifically, with prior art devices, the practitioner rotates the foot from its natural, stable orientation to the referenced neutral position, which is not an inherently stable position. Consequently the practitioner must maintain that leg position during the entire measurement process. If that position is not maintained, the foot tends to return to a compensated orientation resulting in an orthotic that produces an over-correction. Such an orthotic can unduly stress the kinetic chain from the ankle through the knee to the hip. The patient then will experience any of a variety of levels of discomfort.

Orthotic Examination Site 50

Figure 5:
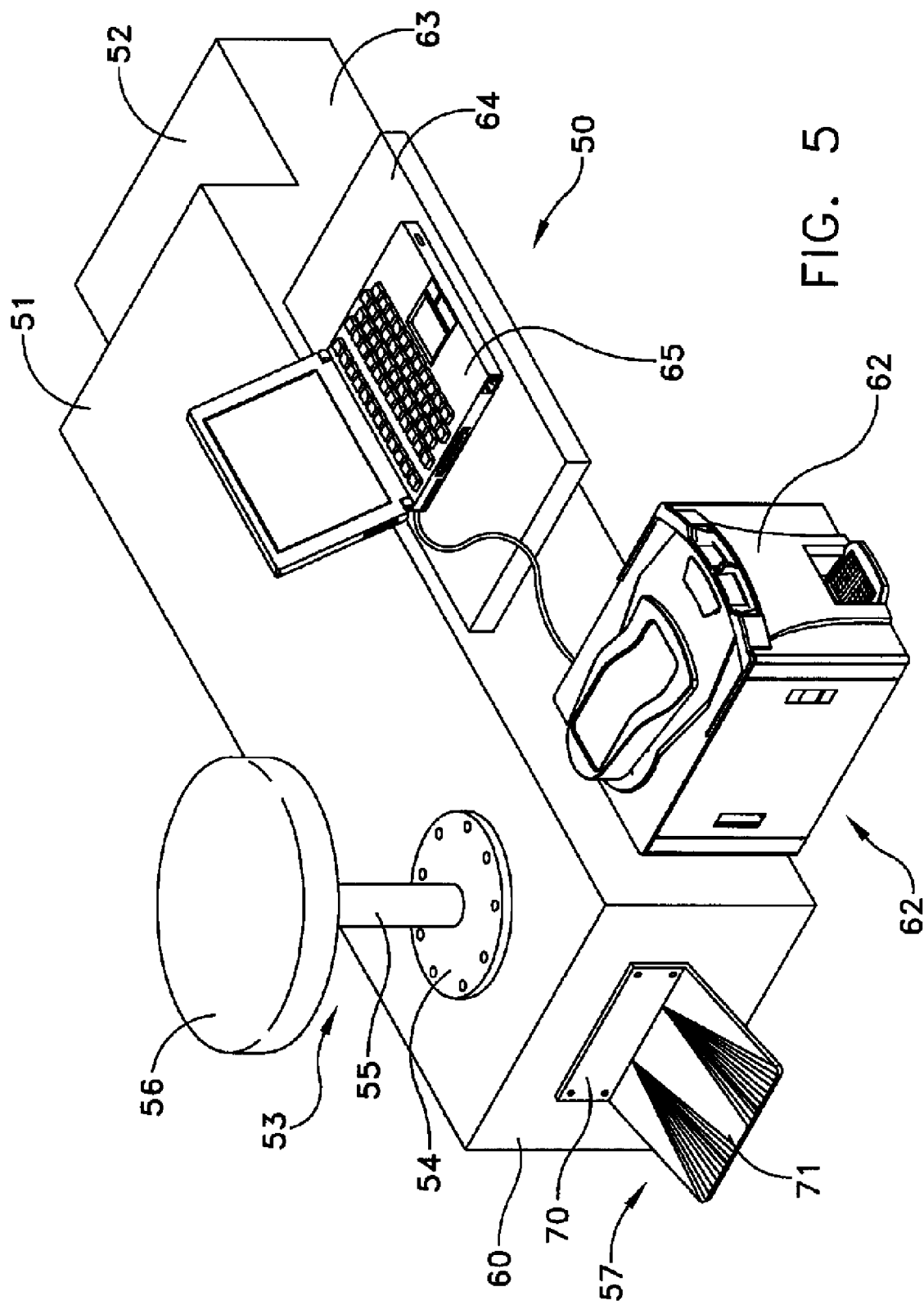
FIG. 5 is a perspective view of one embodiment of an orthotic examination site at which this invention can be implemented.

FIG. 5 depicts an orthotic examination site 50 for measuring the effects of tibial torsion and producing the corresponding information concerning the topography of the bottom of the patient's foot that takes the effects of tibial torsion into account. The orthotic examination site 50 includes an elevated platform 51 with a stair 52 for allowing a patient to climb onto the platform 51. In one specific embodiment the platform 51 is about 50 cm above the floor. The stair may incorporate a rail or other support device.

The platform 51 carries a swivel stool 53 assembly or equivalent structure at the opposite end. The swivel stool assembly 53 includes a plate 54 fixed to the platform 51. A hydraulic lift provides a means for adjusting the height of a seat 56.

The platform structure 51 additionally includes a tibial torsion measurement station 57. The tibial torsion measurement station includes apparatus for measuring a tibial torsion angle for each of the patient's feet. In the embodiment of FIG. 5, this apparatus extends from an end wall 60 of the platform structure 51 opposite to the stair 52. A foot scanner station 61 extends from a front wall 62 of the platform 51. The foot scanner station 61 includes a foot scanner assembly 62 and other apparatus that generate the topographical record of the foot. In the specific embodiment of FIG. 5, the heights of the foot scanner assembly 62 and the platform 51 are approximately the same. A front wall 63 supports a shelf 64 that carries a laptop computer 65 or other embodiment of a control device.

The plate 54 is positioned on the platform to be centered on both the tibial torsion measurement station 57 and the foot scanning station 61. The plate 54 will be spaced from the end wall 60 and the front wall 63 to allow a patient's feet to naturally align with the equipment at each of the stations 57 and 61.

In use, a patient climbs the stair 52 onto the platform 51. The practitioner may have the patient stand on the platform 51 for a physical examination of the patient's feet including such items as arch height. Then the patient will sit on the seat 56 adjusting the height so that the patient's feet are positioned at the proper height for scanning on the foot scanner assembly 62. Once properly seated, the patient will swivel the seat 56 to be aligned with the tibial torsion measurement station 57.

Tibial Torsion Quantification

Figure 6:
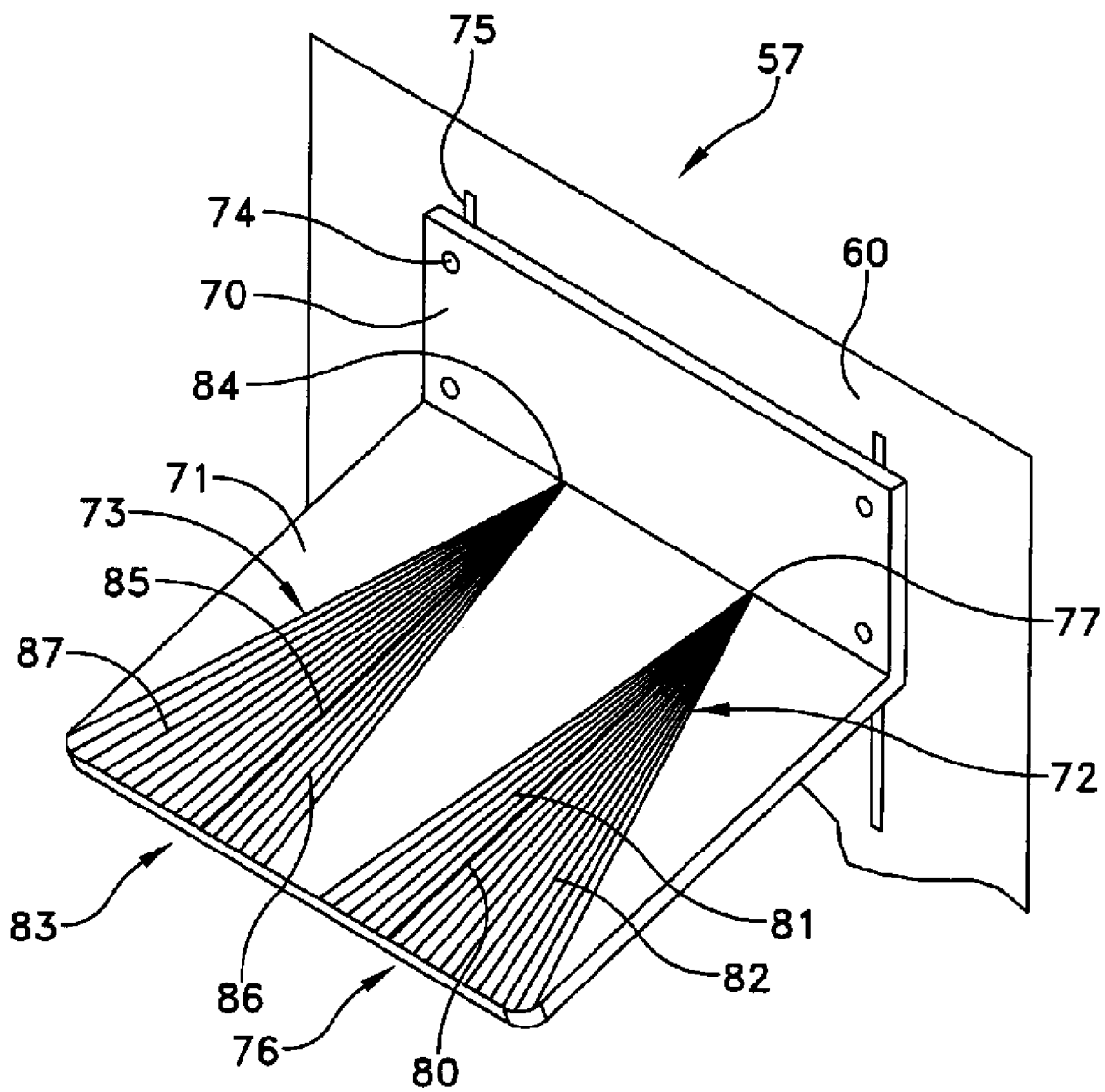
FIG. 6 is a perspective view of a tibial torsion angle measurement station for determining the effects of tibial torsion.

FIG. 6 depicts the tibial torsion measurement station 57 in greater detail. The tibial torsion measurement station 57 comprises a vertical plate 70 that lies in a sagittal plane from which cantilevers a protractor plate 71. "Sagittal", "transverse" and "frontal" are used with conventional meanings in the following discussion.

The protractor plate 71 includes a left protractor 72 and a right protractor 73. A limited array of radial lines 76 extends from an apex 77 and forms the left protractor 72. A reference line 80 corresponds to a 0° tibial torsion angle lies in a sagittal plane. Radial lines 81 that are toward the center from the reference line 77 designate degrees of internal tibial torsion; radial lines 82, degrees of external tibial torsion. Similarly, an array 83 of radial lines extend from an apex 84 of the right protractor 73 to define a 0° reference line 85, internal tibial torsion radial lines 86 and external tibial torsion radial lines 87.

In this specific embodiment, the protractor plate 71 slopes down from the vertical plate 70 by about 10°. An adjustment mechanism, shown as fasteners 74 that engage the vertical plate 70 and extend through slots 75 in the end wall 60 provides a vernier height adjustment for the vertical plate 70.

In the specific embodiment of FIG. 6, the spacing between the reference lines 80 and 85 that represents the average naturally occurring distance between a patients' legs. As will be apparent, the spacing will be an approximation. However, positioning of the feet on the respective fixed position protractors 72 and 73 will have only a minimal impact on the resultant measurement which will be subsequently compensated. Moreover, it will be apparent that any of a variety of known adjustable spacing techniques could be provided for customizing the spacing between the protractors 72 and 73 to a specific patient's natural spacing.

Figure 7:
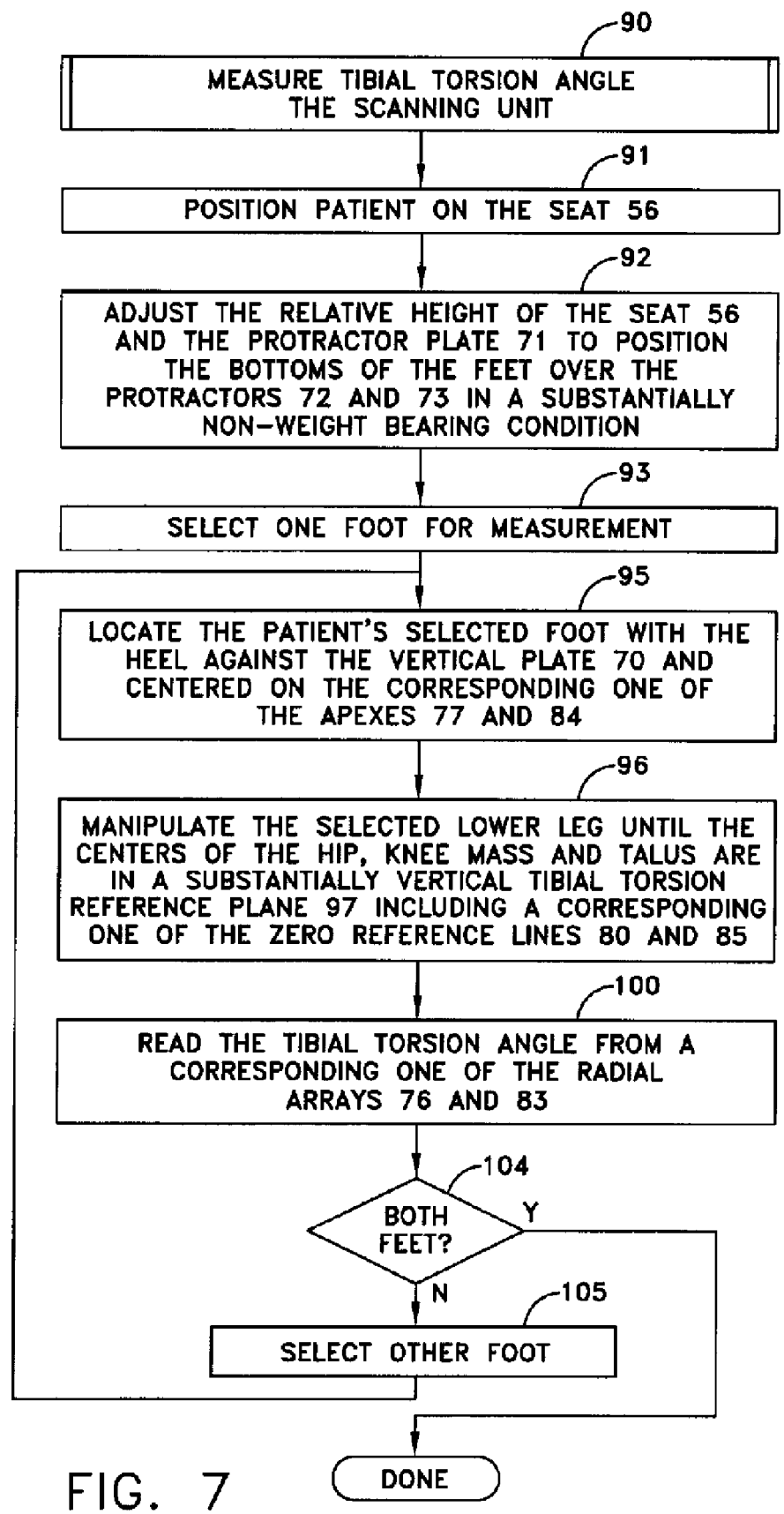
FIG. 7 is a flow chart that depicts the process for determining a tibial torsion angle.
Figure 8:
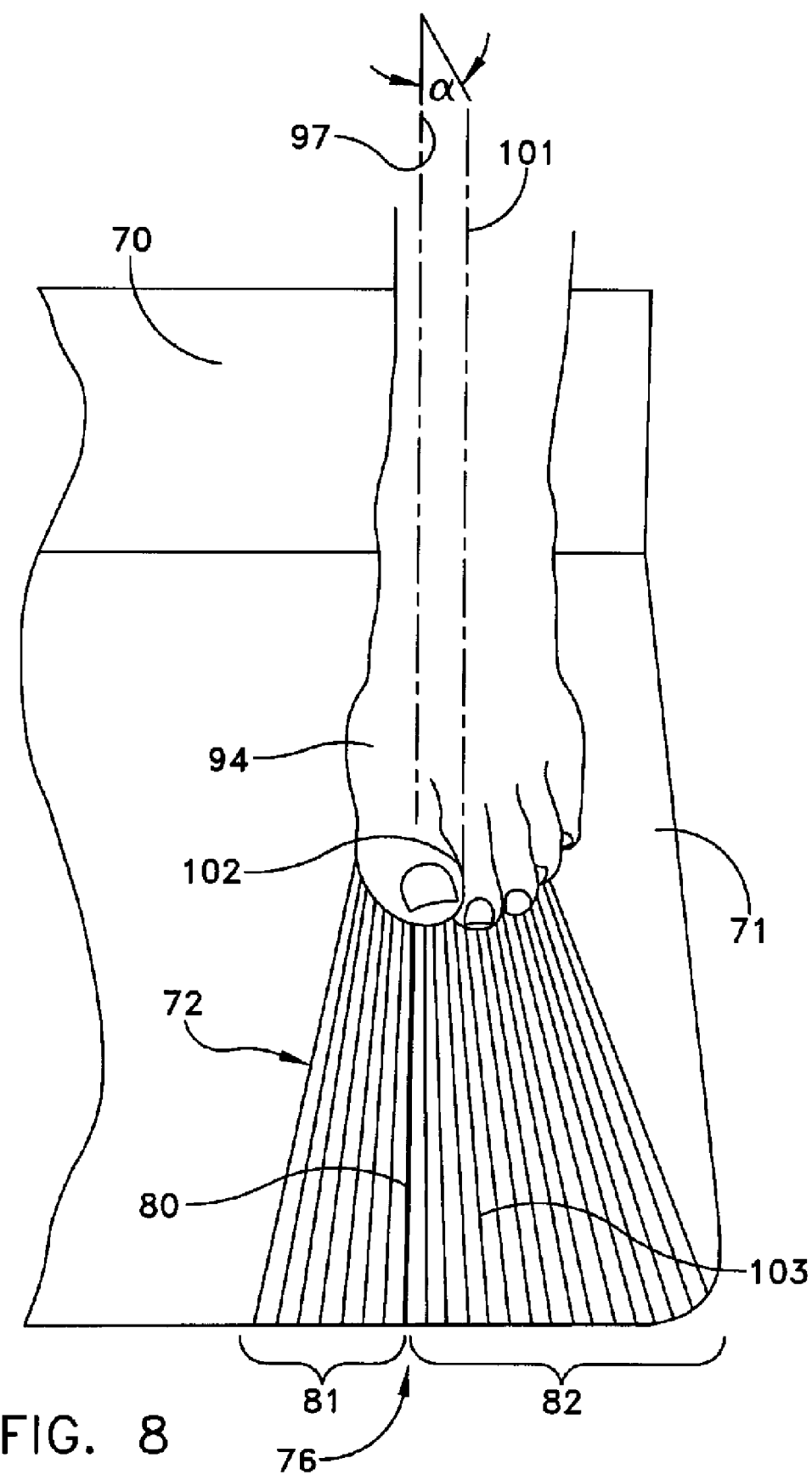
FIG. 8 is a front perspective view of a portion of the tibial torsion angle measurement station of FIG. 6 with the right foot of FIGS. 4A and 4B.

The steps for measuring the tibial torsion angle of a patient's feet are described in FIG. 7 taken in conjunction with FIGS. 6 and 8. FIG. 8 depicts a patient's left foot 94 on the protractor plate 71 over the left protractor 72. The process 90 for measuring the tibial torsion angle begins at step 91 by seating a patient on the stool assembly 53 and positioning the patient's feet on the protractors 72 and 73. In step 92, the practitioner uses a combination of seat height adjustment provided by the height adjuster 55 and vernier adjustment hardware 74 to position the protractor plate 71 to just abut the bottoms of the patient's feet. As the protractor plate 71 slopes down from the vertical plate 70, a patient's feet rest lightly on the protractors 72 and 73 in an essentially non-weight bearing condition.

Next, the practitioner selects a foot for measurement in step 93. For purposes of explanation, assume that the selected foot is the left foot 94 as shown in FIG. 8. In step 95 the practitioner locates the selected foot with the heel against the vertical plate 70 and centered at the apex 77 which is hidden in FIG. 8.

Next, the practitioner uses step 96 to position the selected lower leg until the centers of the hip, knee mass and talus for that leg are included in a substantially vertical plane that constitutes a tibial torsion reference plane 97. Preferably the tibial torsion reference plane 97 includes the 0° reference line for the selected foot, such as the 0° reference radial 80 for the left foot 94 in FIG. 8. In step 100 the practitioner reads the tibial torsion angle, $\alpha$, from the left radial array 76. In theory this radial lies in a tibial torsion measurement plane. The tibial torsion measurement plane preferably is a vertical plane 101 inclusive of the alignment axis 38 that extends from the center of the talus 26 through an interstice 102 between the patient's first and second toes. As will be apparent, however, the apexes, such as the left apex 77, are not located under the center of the talus 26. They are offset to the back of the heel at the vertical plate 70. However, the assumption that the apexes 77 and 84 are centered on their respective taluses does not introduce any significant mathematical error for small angles. However, placing the apexes 77 and 84 at the back of the protractor plate 71 facilitates that foot placement because the practitioner can see the apexes 77 and 84 even with only a minimal displacement of the heels from the vertical plate 70.

In FIG. 8, a radial line 103, representing the tibia torsion angle of about 4° extends through the interstice 102. The radial line lies in the tibial torsion measurement plane 101 so the radial line 103 provides a measurement of the angular displacement between the tibial torsion reference plane and the tibial torsion displacement plane that is inclusive of the center of the talus and the interstice of the first and second toes of the patient's foot. In this figure, the measurement shows that the patient has 4° of external tibial torsion.

When this step 100 is completed, and if both feet have been selected, the process is complete. Otherwise in accordance with steps 104 and 105 the practitioner selects the other foot and performs the operations of steps 95, 96 and 100 to obtain the measurement of the angular displacement between the tibial torsion reference plane and the tibial torsion displacement plane for that foot.

When the practitioner completes the measurement process shown in FIG. 7, the practitioner has an approximate quantification of the effects of tibial torsion on each foot. These measurements may deviate from absolute measurements involving the theoretical sagittal plane 97 through the talus and a vertical tibial torsion measurement plane 101 due to visual inaccuracies in determining that the leg lies exactly in a vertical plane. However, such deviations will be small. Given the orientation of the actual planes corresponding to planes 97 and 101, such errors are not mathematically significant to the ultimate scan that is obtained at the foot scanning station 61 of FIG. 6.

The Foot Scanner Assembly 62

Figure 9:
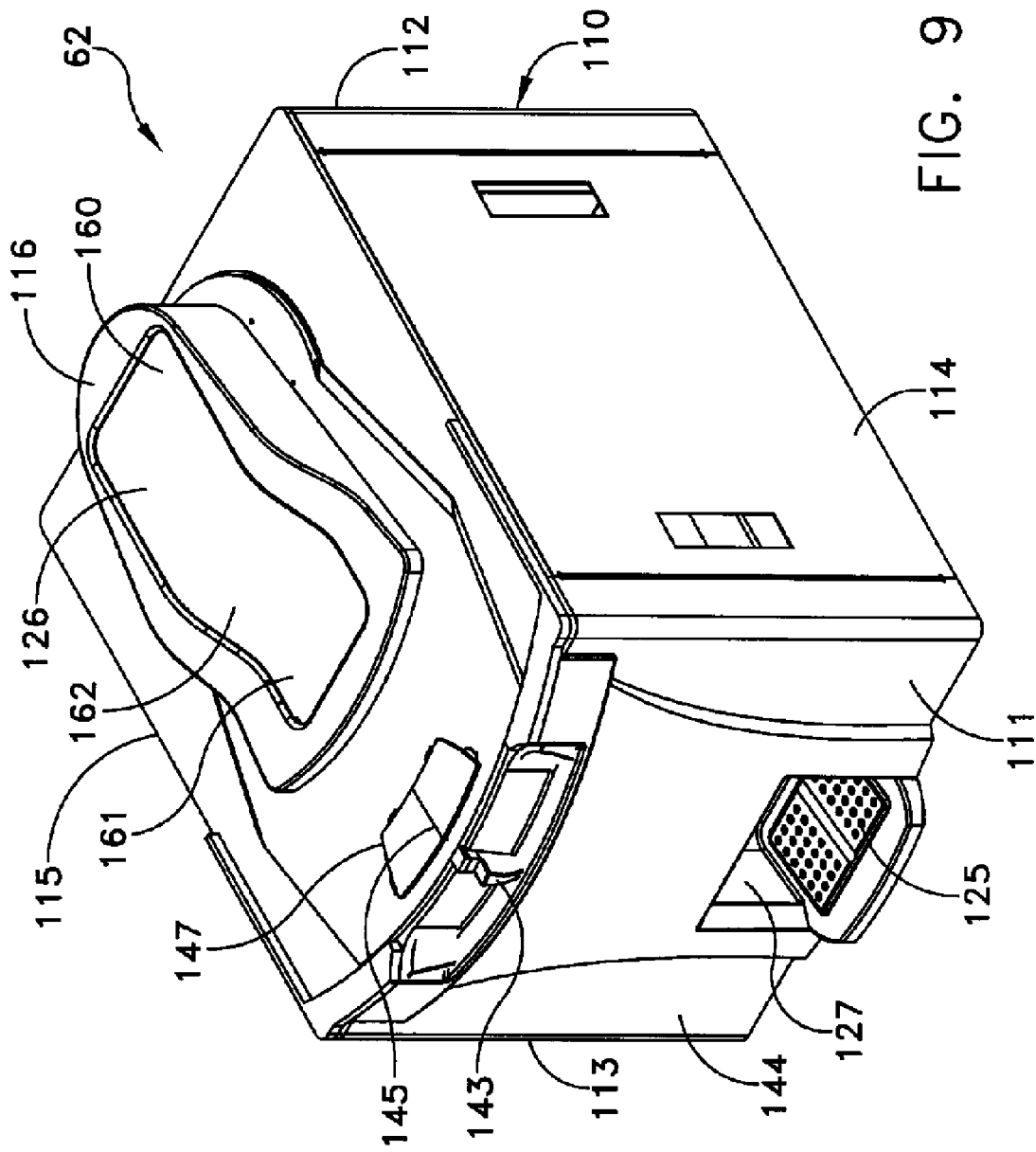
FIG. 9 is a perspective view of a foot scanner assembly for use at a scanning station of the orthotic measurement site in FIG. 5.
Figure 10:
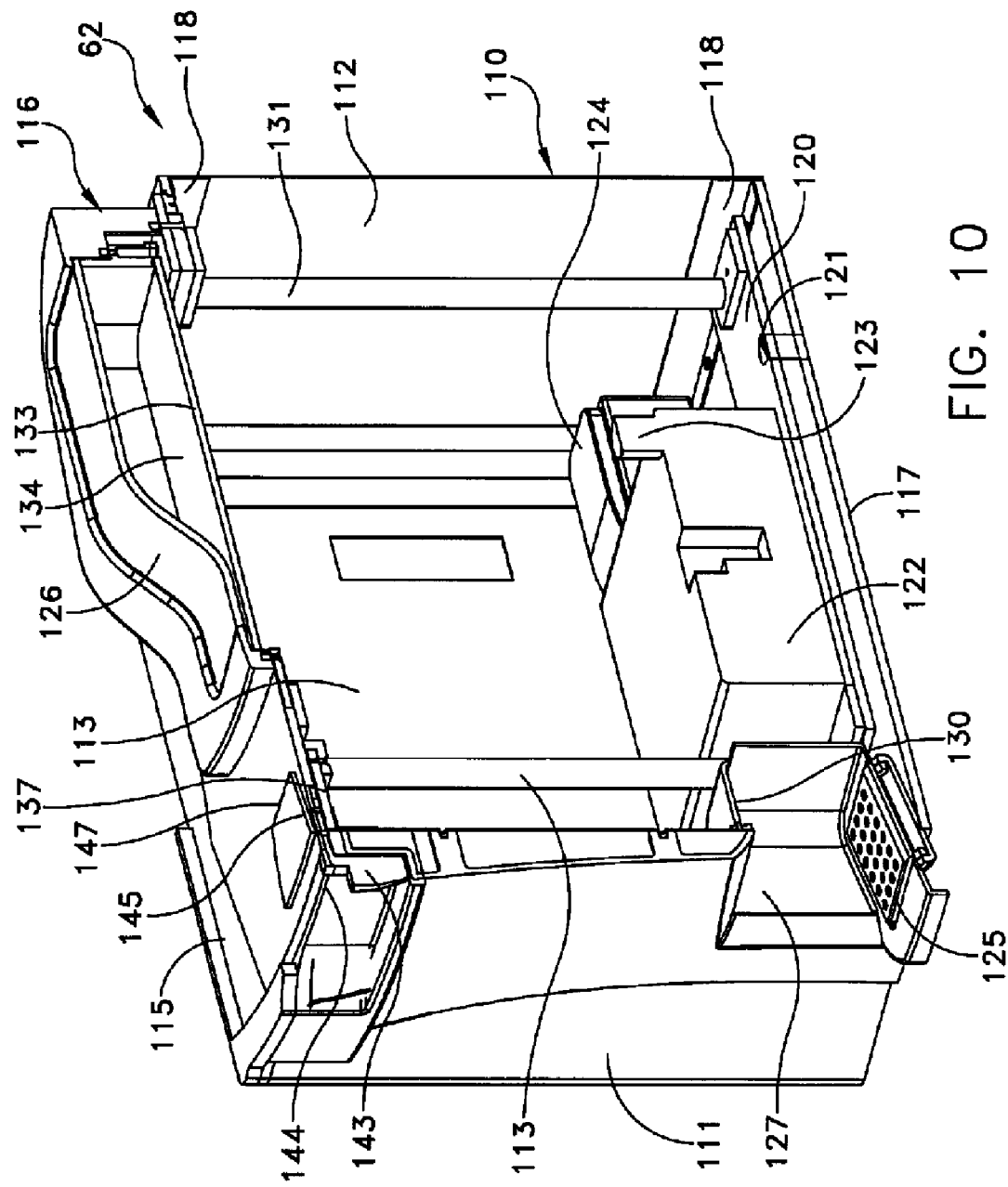
FIG. 10 is a perspective view of a section of the foot scanner assembly in FIG. 9.
Figure 11:
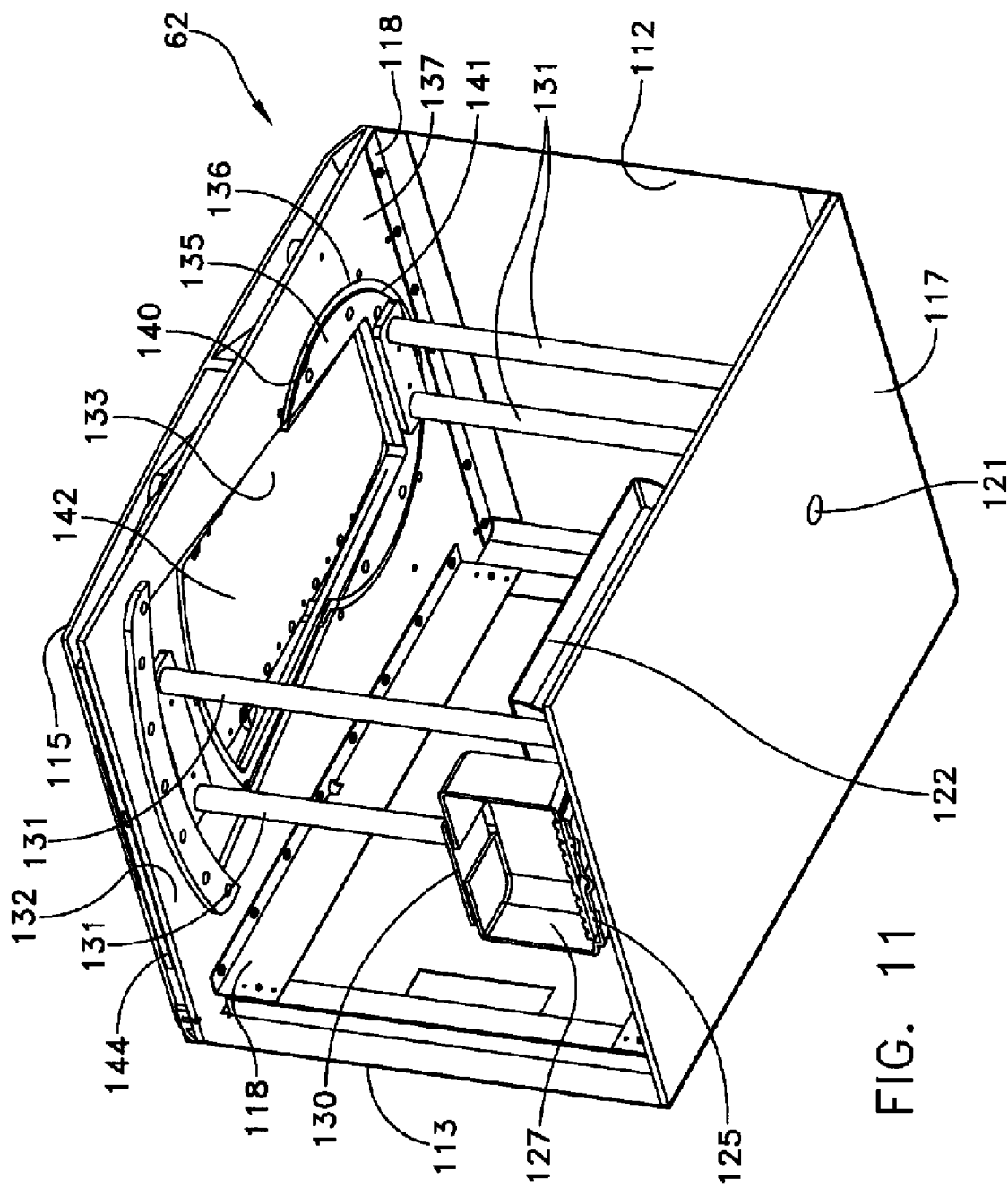
FIG. 11 is another perspective view of the foot scanner assembly in FIG. 9 with certain portions removed.

A specific embodiment of a foot scanner assembly 62 as shown in FIGS. 9 through 11 includes a housing 110 formed by a front cover 111, a rear cover 112, a left side cover 113 and a right side cover 114. In this embodiment a top cover 115 surrounds a pivotally mounted air cushion 116. The structural members of this foot scanner assembly 62 include a base 117 that is supported on the floor. A framework 118 mounts to the base 117 to support the various covers.

Now referring to FIGS. 10 and 11, the base 117 carries a pivot plate 120 mounted on a pivot 121 at the base 117 so that the pivot plate 120 can swing about the pivot 121 for a range of angles. The pivot plate 120 carries a three-dimensional laser scanner 122 with a scanning port 123 and an air pump 124. The air pump 124 inflates the air cushion 116 when the practitioner moves an "on-off-on" rocker switch 125 to an "inflate" position. Inflating the air cushion 116 expands a flexible membrane 126. In the other "on" or "deflate" position, the switch 125 operates an electrically-operated pressure relief valve to deflate the air cushion 116. Such a pressure relief valve is not shown in the figures, but is well known in the art. The switch 125 is located in a cavity 127 formed at the bottom of the front cover 111.

In this specific embodiment a toe-operated switch 125 at the top of the cavity 127 initiates the operation of the laser scanner 122. The switches 125 and 130 and supporting structure are mounted on the base 117 so each is fixed relative to the front cover 111 and cavity 127.

The pivot plate 120 serves as a base for a pivotable structure that includes vertical columns 131. The vertical columns carry an upper plate 132. The upper plate 132 carries a transparent plate 133. The top surface of the transparent plate 133 constitutes a transverse reference plane 134 as shown in FIG. 10.

The upper plate 132 additionally carries a disk 135 on its bottom side that lies in an opening 136 formed in a top plate 137 spaced below the top cover 115. An inner edge 140 of the opening 136 provides a bearing surface for an edge 141 of the disk 135. A sector opening 142 in the top plate 137 frees the structure to rotate over a limited range. In one embodiment, the total range is about 20°.

A handle or tab 143 extends from the top plate 137 through a passage 144 between the top cover 115 and top plate 137. The practitioner uses this tab 143 to position the angular orientation of the upper plate 132 with respect to the front of the structure. An indicia 145 visible through a window 147 with indicia provides a visual indication of the angular orientation.

FIGS. 9 through 11 depict the foot scanner assembly 62 with the air cushion 116 in an angularly centered, or reference, position. With the foregoing construction, the practitioner uses the tab 143 to pivot the air cushion about a vertical axis through the pivot 121 and the center of the disk 135. More specifically, given the integral construction of the pivot plate 120, pivot 121 with the laser 122, air pump 124 and columns 131 that connect to the upper plate 132, moving the tab 143 causes the air cushion 116, laser scanner 122 and air pump 124 to rotate simultaneously.

Figure 12:
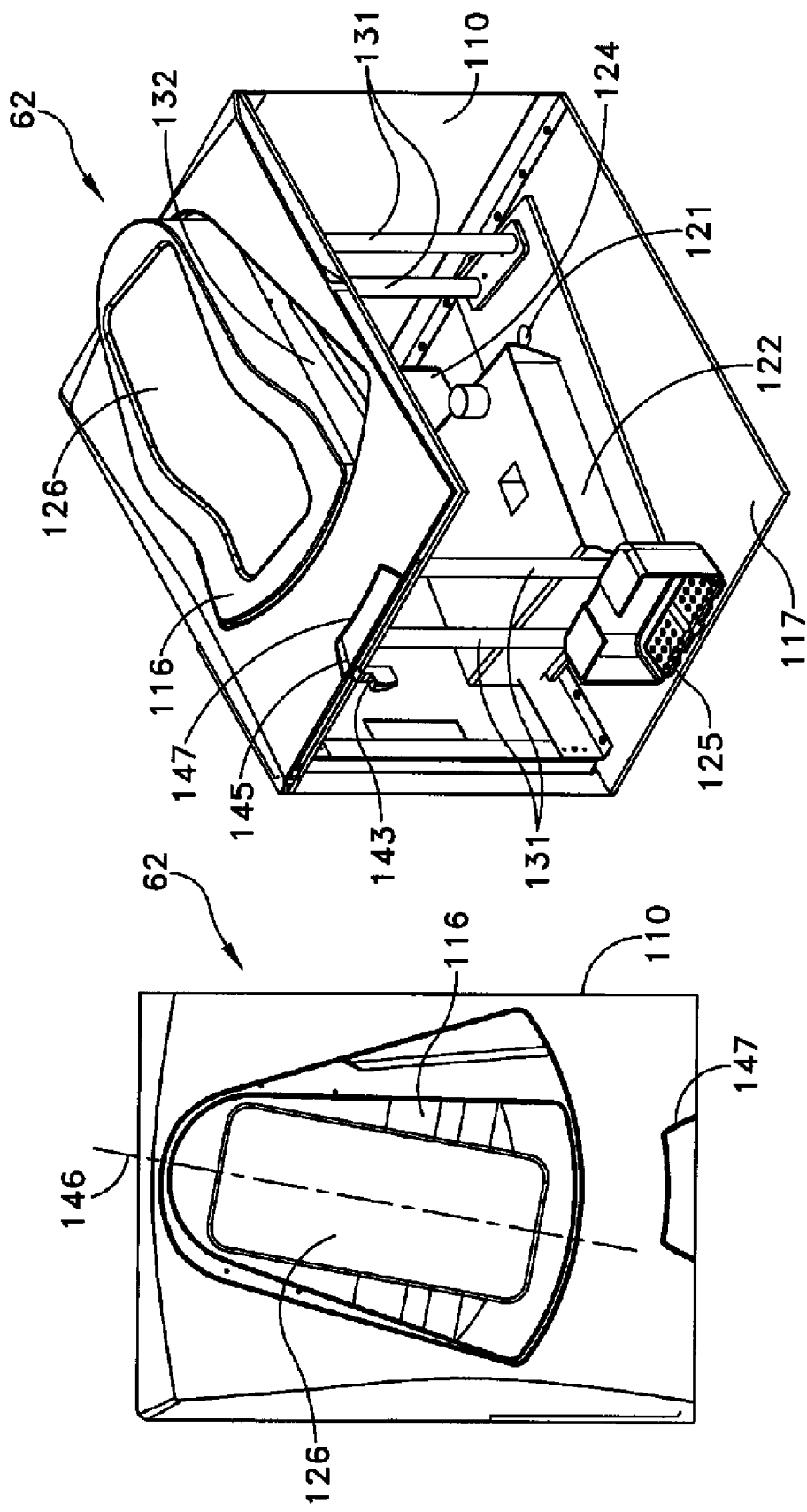
FIG. 12A is a top view of the foot scanner assembly of FIG. 9 with the foot scanner rotated clockwise.
FIG. 12B is a perspective view of the foot scanner assembly of FIG. 12A with the front and side covers removed.

FIGS. 12A and 12B depict the foot scanner assembly 62 after a practitioner has moved the tab 143 to a full clockwise limit. In this particular embodiment this represents about a 10° range. As a result a scanning axis 145 that extends longitudinally through the center of the air cushion 116 rotates 10° clockwise.

Figure 13:
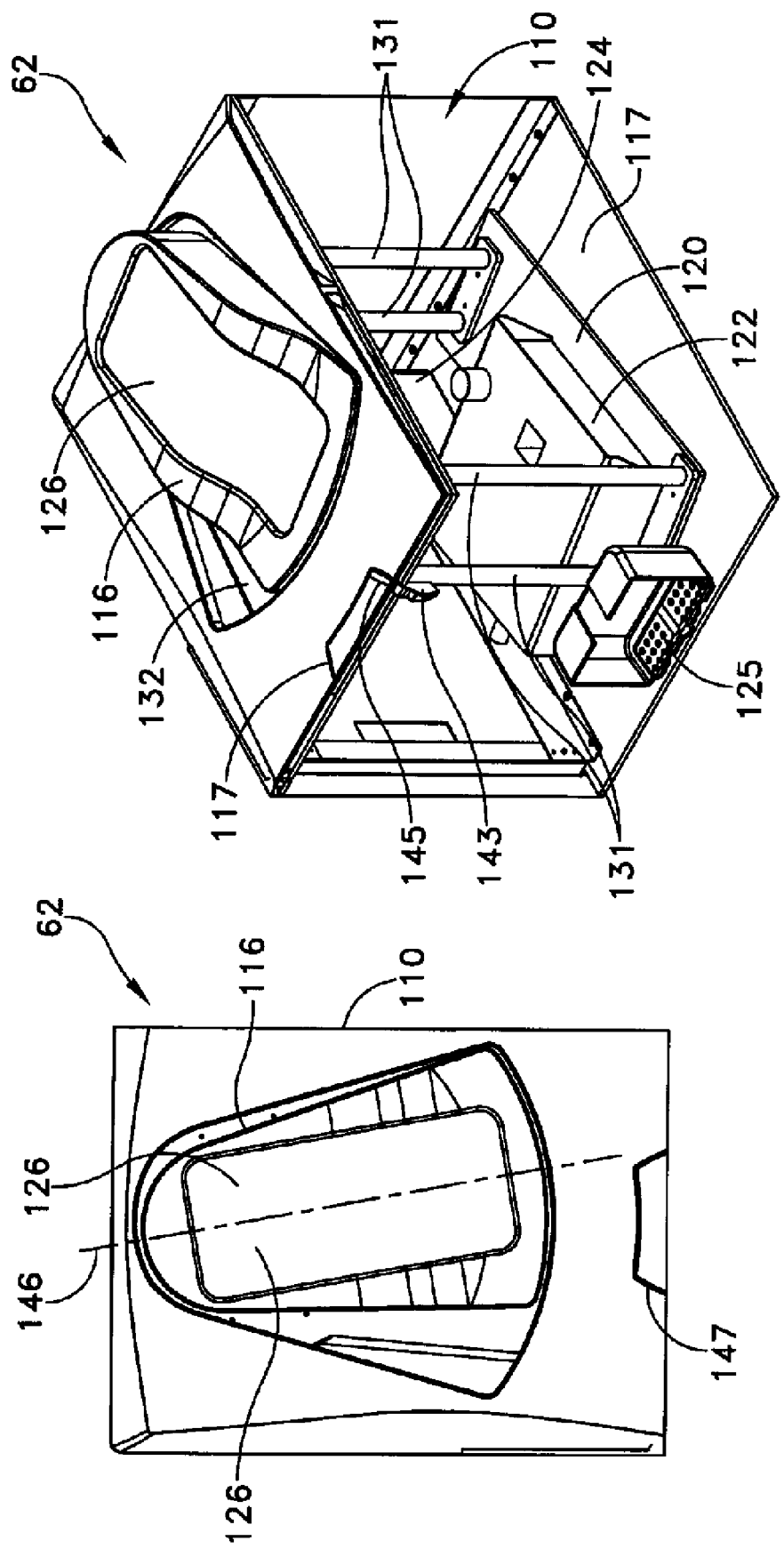
FIG. 13A is a top view of the foot scanner assembly of FIG. 9 with the foot scanner rotated counterclockwise.
FIG. 13B is a perspective view of the foot scanner assembly of FIG. 13A with the front and side covers removed.

Similarly, if the practitioner moves the tab 143 in a counterclockwise direction or to the right from the front of the foot scanner assembly 62 as shown in FIGS. 13A and 13B, the air cushion 116 rotates about the pivot 121 (hidden in FIG. 13B), again carrying the air cushion 116, laser scanner 122 and air pump 124. At each point, the specific angle of rotation is shown in the indicia 146.

Figure 16:
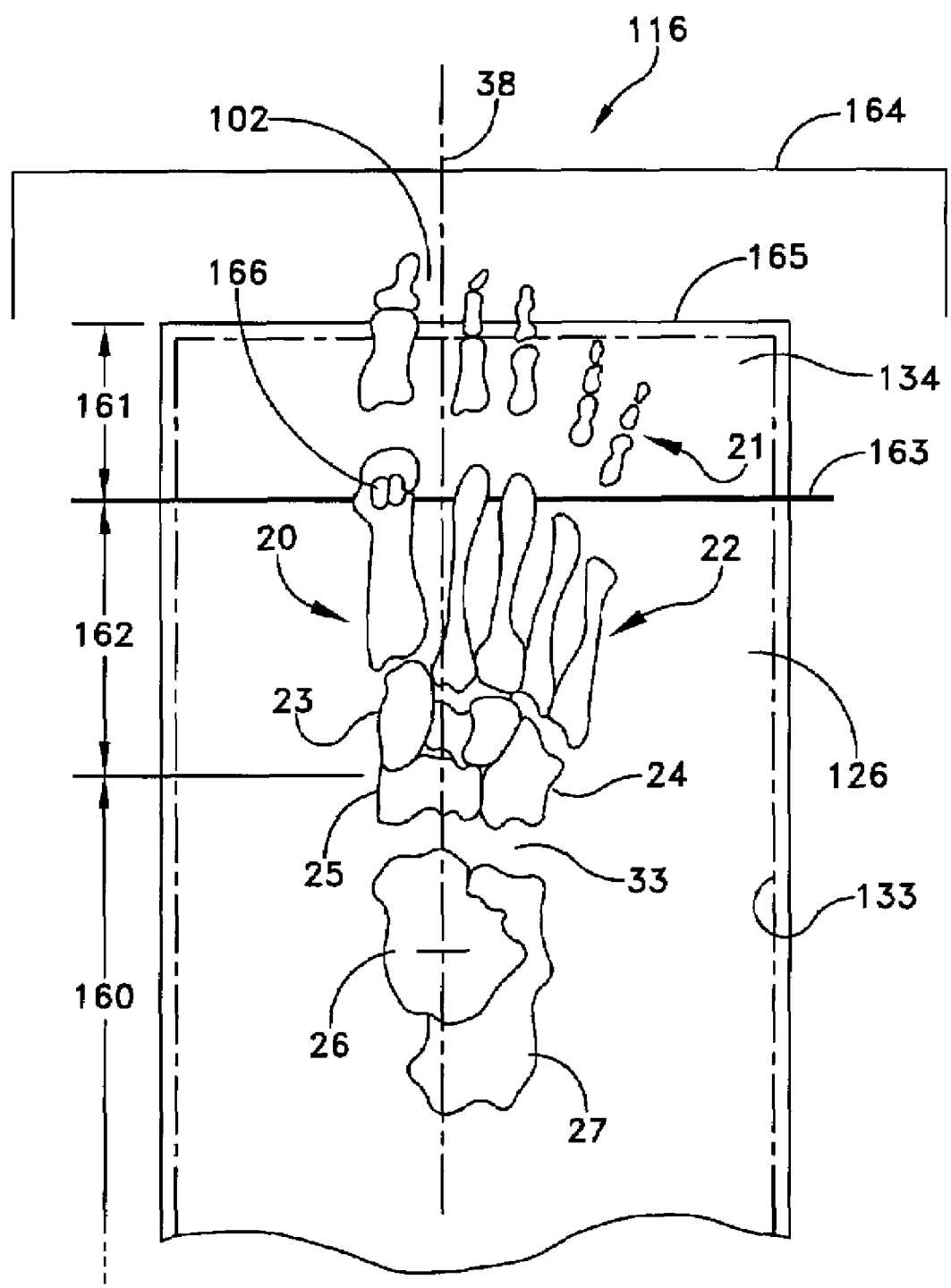
FIG. 16 depicts a foot located on a foot scanner incorporated in the foot scanner assembly of FIG. 9.

The air cushion 116 in FIGS. 9 and 10 has the same basic construction as is disclosed in U.S. application Ser. No. 11/116,738. As shown in FIG. 16, the patient's foot supported at the reference plane 134 defined by the top of the transparent plate 133 when the air cushion 116 is deflated. A portion 160 of the membrane 126 that lies under the rear foot is relaxed. A portion 161 of the membrane 126 under the phalanges is under a slight tension. An intermediate portion 162 provides a ramp or transition between the lower forefoot portion 161 and the upper rear foot portion 160. As a result, the air cushion 116 acts as a variable volume, sealed chamber bounded by the transparent plate 133 and the membrane 126. When the air pump 124 increases the pressure within a chamber, the membrane 126 stretches with the portion 160 tending to expand before the transition portion 162.

The membrane 126 may include an additional reference for aiding the practitioner's placement of a patient's foot in the form of a placement line 163 extending across the top of the flexible membrane 126 so it is visible to the practitioner. This line 163 is parallel to a front wall 164 and positioned to the rear of the front edge 165 of the transparent plate 133 and corresponds to the boundary between the stretched and relaxed portions of the flexible membrane 126.

Operation of Foot Scanner Assembly 62

With this background of the construction and operation of the specifically disclosed foot scanner assembly 62, it will now be possible to describe a measurement process by which a practitioner acquires the information about the patient's foot. The process begins by initiating a session as represented by step 150 in FIG. 14. A "session" can include a procedure for a single patient or multiple patients seen in some time period, such as a day.

The first procedure, as represented by steps 151 and 152, involves gathering and storing patient information including the process of measuring the tibial torsion angle for the patient's feet as described with respect to FIGS. 6 through 8. More specifically, the practitioner interviews the patient to obtain bibliographic information, medical information particularly related to foot evaluation, lower body alignment, gait evaluation, footwear evaluation and other relevant information.

Then the practitioner has the patient sit on the seat 56 in FIG. 5 to obtain the tibial torsion measurements at the tibial torsion measurement station 57. When this information has been obtained and entered, the patient swivels the seat 56 in FIG. 5 to position his or her feet at the foot scanner station 61.

Figure 14:
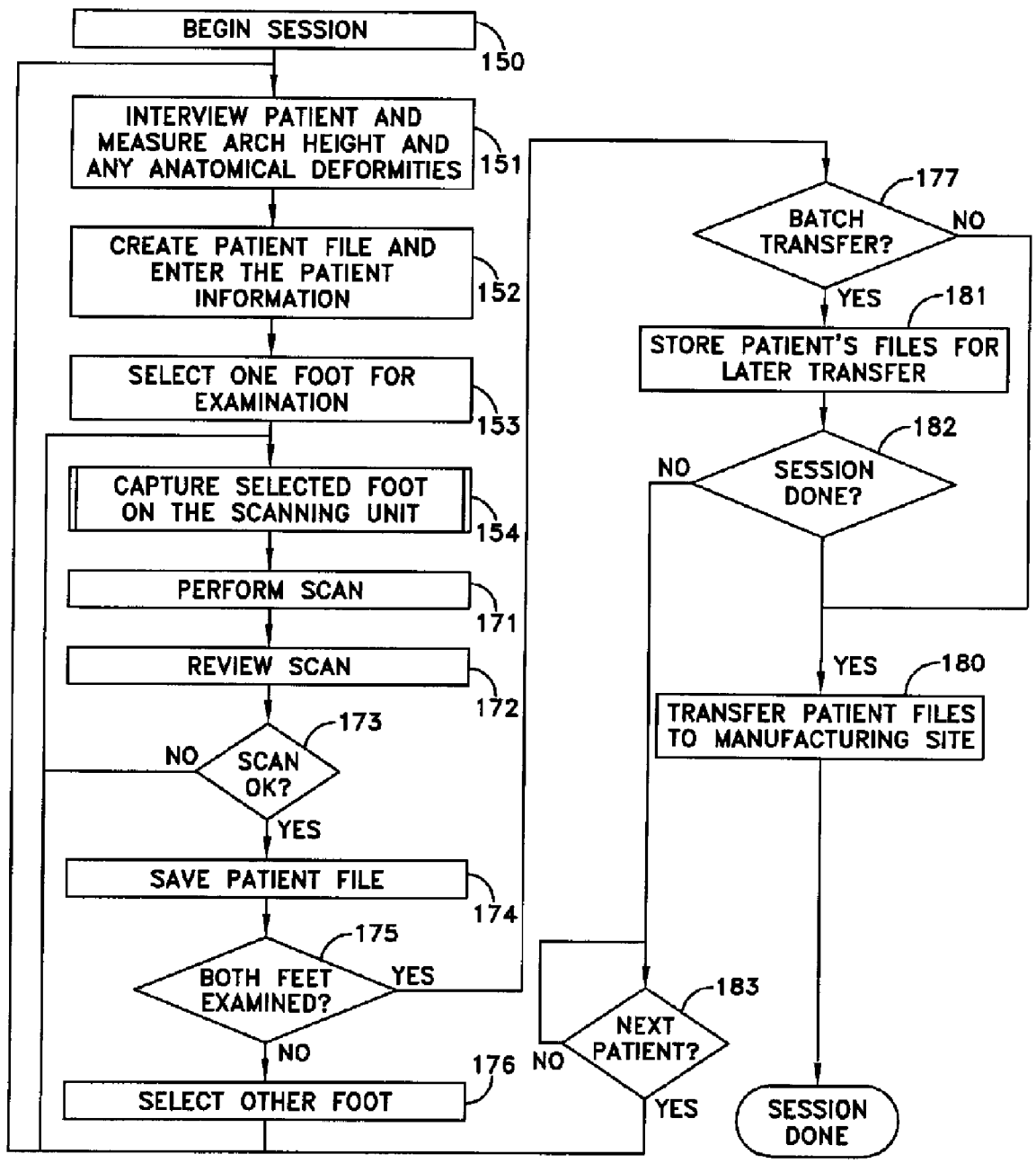
FIG. 14 is a flow diagram of the process for examining a patient on the foot scanner assembly.
Figure 15:
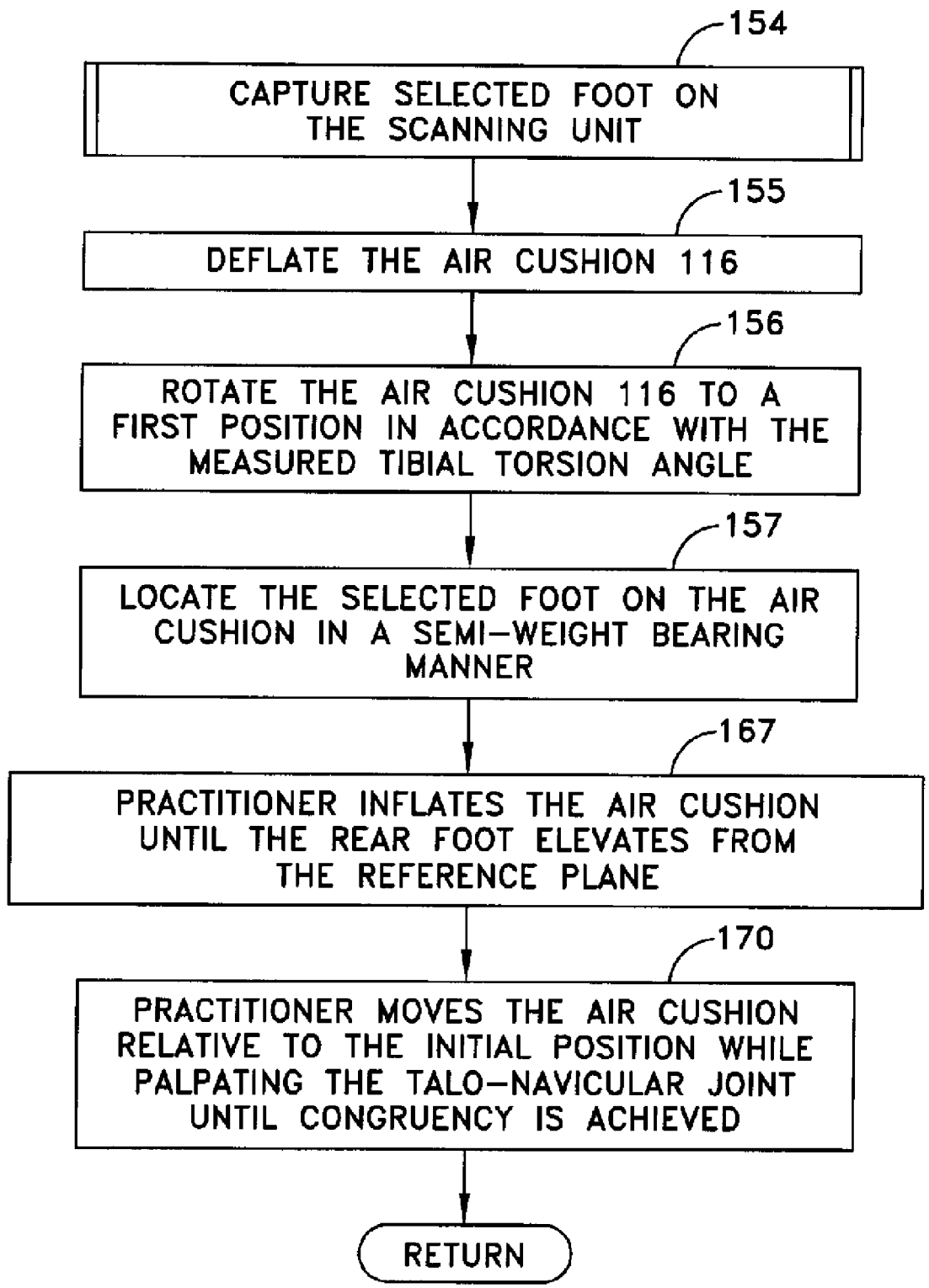
FIG. 15 is a flow diagram for a foot capture process used in the process of FIG. 14.

In step 153 in FIG. 14 the practitioner selects one foot for capture by a procedure 154 shown in greater detail in FIG. 15. More specifically, the procedure 154 captures the selected foot in a referenced neutral position with the forefoot and midfoot locked against the rear foot taking the effect of any tibial torsion into account More specifically, assuming that the right foot is selected, the practitioner deflates the air cushion 116 by depressing the "deflate" side of the rocker switch 125 to activate the pressure release valve at step 155.

In step 156 the practitioner grasps the tab 143 shown in FIG. 9 to rotate the air cushion 116 about the pivot point 121 until a tibial angle indicia in window 147 matches the measured tibial torsion angle. This moves the air cushion 116 into a first angular position at which the air cushion 116 will be inflated.

Step 157 represents the process by which the practitioner locates the selected foot on the air cushion 116 with the alignment axis 38 aligned with longitudinal axis through the air cushion 116; and this longitudinal axis is offset by the measured tibial torsion angle. More specifically, as shown in FIG. 16, the practitioner aligns the foot so that the first-metatarsal-phalanges joint 166 (i.e., the big toe joint) is centered on the line 163 and with the alignment axis 38 perpendicular to the line 163. The practitioner also locates the patient's leg in a substantially vertical plane thereby to bring the foot into a position that approximates or even achieves talo-navicular congruency. Consequently the foot does not pronate or supinate as described with reference to FIGS. 4A and 4B because the air cushion 116 has been pivoted to the first position.

Step 167 represents the action of the practitioner in operating the air pump 124 to inflate the air cushion 116 while observing the position of the heel. As the pressure in the air cushion 116 increases, the membrane 126 molds to the plantar fascia surface with equal pressure. Moreover, as the membrane 126 has a width that is greater than the width of a foot, the membrane 126 begins to move up along the sides of the foot. When the membrane 126 lifts the heel off the reference plane 134, the air cushion "captures" the foot. During this operation the practitioner may palpate the talar heads to gain some foresight for use in the next step of the process.

Step 170 represents the action of the practitioner in manipulating the air cushion 116 about the first position to move the foot to the referenced neutral position while the foot is captured in the air cushion 116. Basically the practitioner then palpates the talar heads as the air cushion 116 pivots to a measurement position at which the heads are even. At this point the talus 26 and the navicular 25 in FIG. 1 are congruent, and the subtalar joint 32 is in a neutral position.

There are several alternatives for performing this step. A practitioner will adopt a process that is most comfortable. For example, if the effects of tibial torsion are small, the practitioner may merely manipulate the leg to active congruency. Where the effects are greater, the practitioner may palpate the talus while incrementally pivoting the air cushion 116 until the talar heads are even. As an example of another approach, the practitioner might hold the leg in a vertical position and then release the leg observing any motion to one side or the other. If the leg falls away from the middle, the practitioner would move the tab toward the center. Conversely, if the leg falls toward the middle, the practitioner would move the tab away from the center. These tests would continue until the leg remained in a stable position.

By whatever one of the foregoing or other approaches that a practitioner might implement, the practitioner moves the air cushion to a measurement position that may or may not be the same as the first position. What is important, however, is that in this measurement position, the foot is in an ideal and stable position.

As previously indicated, however, it may not be possible to move a foot of some patients to this neutral position without discomfort and without supination or pronation. In that situation the practitioner may elect to move the foot only partially toward this referenced neutral position. Unlike prior art approaches, however, the alignment axis 38 still is offset to accommodate tibial torsion.

The stability of the foot in the air cushion 116 at the measurement position provides an important advantage. This stability allows the practitioner to release the leg and foot during a scan. That is, once the foot is captured, the examination process returns to step 171 in FIG. 14 whereupon the practitioner initiates the scan. In the specifically disclosed embodiment this occurs when the practitioner activates the toe switch 130. The laser scanner 122 scans the bottom of the patient's foot represented by the bottom surface of the membrane 126 through the transparent plate 133.

Once the scan is completed, which is a matter of only a few seconds, the practitioner displays the scan on the control system 65 for review in step 172. Typically the practitioner will look to see that the scan has a maximum distance at about the center of the heel and that heel is presented with a rounded appearance. If the practitioner is not satisfied with the scan, then, as shown by step 173, the practitioner recaptures the foot in the procedure 154 and repeats the scan and review processes of steps 171 and 172.

When the practitioner is satisfied the scan, the practitioner saves the scan as a patient file for the selected foot as represented by step 174. If the practitioner needs to examine the other foot, the procedure passes from step 175 to step 176 for selecting the other foot. Then the practitioner repeats the capture process 154 and the scan and review steps 171 and 172. If both feet have been examined, the practitioner transfers the patient's files to a local or remote manufacturing site.

When the manufacturing facility is local to the orthotic examination site 50 in FIG. 5 each patient's files can be transferred to the local manufacturing site when they are saved. Alternatively, if a plurality of orthotic examination stations, like the orthotic examination station 50, are networked to a common manufacturing site, it may be desirable to save the individual files at the orthotic examination station 50, such as in the control site 65, for a periodic transfer, such as a daily transfer, from the orthotic examination station to the manufacturing facility site.

Referring again to FIG. 14, step 177 represents a process by which the operation passes control to step 180 for transferring patient files to the manufacturing facility and completion of the session. If batch transfers are to be made, such as at the end of a business day, the files are stored locally for later transfer as in the control system 65 or other storage facility at the orthotic examination station 50, as represented by step 181. When the session is then completed, steps 182 and 180 make the transfer of all the patient files to the manufacturing facility. If the time has not arrived for such a transfer, step 183 represents a step for waiting for a next patient examination to begin. Then the process starts at step 151.

Thus, the manufactured orthotic footbed provides proper support for an individual's foot and, because a tibial torsion angle has been measured and incorporated in the generation of the topography of the individual's foot, accommodates the effects of tibial torsion without overcorrection. Such orthotic footbeds are obtained by measuring a tibial torsion angle for each of a patient's feet through the tibial torsion measurement station 57, particularly by means of the protractor plate 71 and the protractors 72 and 73. A foot measurement device in the form of a scanner can then be moved to a first position whereby an alignment axis is displaced from a central position by angle corresponding to the measured tibial torsion angle, such as provided by the structure involving the base plate 117 and related structure including the air cushion 116 to the measured tibial torsion angle between the two limits shown in FIGS. 12A and 13A. The air cushion 116 constitutes one embodiment of a structure that then captures the foot in the foot measurement device. Shifting the pivotal structure by manipulating the tab 143 with palpation of the ankle allows the practitioner to position the foot so that the talus and navicular exhibit congruency thereby to establish a measurement position. The laser scanner 122 constitutes a structure for the generating a three-dimensional laser scan of the bottom of the membrane 126 with the resulting recorded information constituting a topographical record of the foot. In one particular application this information is used directly for the production of an orthotic footbed.

This invention has been described in terms of specific implementations of a tibial torsion measurement apparatus and foot scanner for the production of orthotic footbeds. It will be apparent to those of ordinary skill in the art that a number of variations can be made. For example, the tibial torsion protractor is shown as being constructed of a single plate. The individual functions for the left and right feet could be implemented by separate protractor structures that would incorporate vernier height adjustment. It might also include vernier width adjustment. A specific foot scanner has been shown, but this invention is applicable to a variety of foot scanners. Moreover the disclosed foot scanner has certain advantages over other foot scanners. However, modifications could be made to the specifically disclosed foot scanner as by changing the specifically disclosed mechanisms for rotating the air cushion, while still obtaining the objectives and advantages of this invention. Further, specific dimensions have been given by way of example. Devices with other dimensions could be substituted.

Therefore it is the intent of the appended claims to cover all such variations and modifications as come within the true spirit scope of this invention.

What is claimed is:

1. A method for producing a custom orthotic footbed for a patient's footwear by generating a representation of the topography of the bottom of the patient's foot on a foot scanner adapted to pivot from a reference position, said method comprising the steps of:
   A) measuring a tibial torsion angle for the patient's foot,
   B) pivoting the foot scanner from the reference position to a first position by an angle corresponding to the measured tibial torsion angle,
   C) capturing the foot in the foot scanner at the first position,
   D) manipulating the foot scanner transversely proximate the first position until the patient's talus and navicular exhibit congruency thereby to establish a measurement position, and
   E) generating the topographical record of the foot with the foot scanner in the measurement position for use in the production of the custom orthotic footbed.

2. A method as recited in claim 1 wherein said measurement is made with the patient's leg in an essentially non-weight bearing condition.

3. A method as recited in claim 2 wherein said capture and manipulation of the toot and generation of the topographical record are made with the patient's foot in a semi-weight bearing condition.

4. A method as recited in claim 3 wherein said tibial torsion angle measurement includes:
   i) positioning the patient's leg in a tibial torsion reference plane inclusive of the centers of the patient's hip, knee mass and talus, and
   ii) measuring a tibial torsion angle as the angular displacement between the tibial torsion reference plane and a tibial torsion displacement plane inclusive of the center of the talus and the interstice of the first and second toes of the patient's foot.

5. A method as recited in claim 4 wherein said foot scanner manipulation includes angularly oscillating the foot scanner about an axis of rotation and said capture includes positioning the patient's foot with the center of the talus substantially aligned with the axis of rotation.

6. A method as recited in claim 5 wherein said foot scanner angular oscillation continues until the patient's talus and navicular exhibit congruency.

7. A method as recited in claim 3 wherein said foot scanner includes an air cushion for capturing the patient's foot and means for deflating and inflating the air cushion, said capturing of the foot including positioning the foot on the air cushion in a deflated state and inflating said air cushion to elevate the patient's heel with the foot scanner in the first position.

8. A method as recited in claim 7 wherein said foot scanner manipulation includes angularly oscillating the foot scanner about an axis of rotation and said capture includes positioning the patient's foot with the center of the talus substantially aligned with the axis of rotation.

9. A method as recited in claim 7 wherein said topographical record is obtaining by producing a three-dimensional scan of the bottom of the patient's foot that records the distance from a reference plane to the bottom of the foot for each of an array of positions in the reference plane.

10. A method as recited in claim 1 wherein said tibial torsion angle measurement includes:
    i) positioning the patient's leg in a tibial torsion reference plane inclusive of the centers of the patient's hip, knee mass and talus, and
    ii) measuring a tibial torsion angle as the angular transverse displacement between the tibial torsion reference axis and a tibial torsion displacement plane inclusive of the center of the talus and the interstice of the first and second toes of the patient's foot.

11. A method as recited in claim 10 wherein said foot scanner manipulation includes angularly oscillating the foot scanner about the first position to determine a measurement position at which the talus and navicular of the patient's foot exhibit congruency.

12. A method as recited in claim 11 wherein said foot scanner includes an air cushion for capturing the patient's foot and means for deflating and inflating the air cushion, said capturing of the foot including positioning the foot on the air cushion in a deflated state and inflating said air cushion to elevate the patient's heel with the foot scanner in the first position.

13. A method as recited in claim 12 wherein said topographical record is obtained by producing a three-dimensional scan of the bottom of the patient's foot that records the distance from a reference plane to the bottom of the foot for each of an array of positions in the reference plane.

14. A method as recited in claim 1 wherein said tibial torsion angle measurement includes:
    i) positioning the patient's leg with the centers the patient's hip, knee mass and talus on a tibial torsion sagittal reference plane, and
    ii) measuring a tibial torsion angle the angular transverse displacement between the tibial torsion sagittal reference plane and a vertical tibial torsion displacement plane inclusive of the center of the talus and the interstice of the first and second toes of the patient's toot.

15. A method as recited in claim 14 wherein said foot scanner manipulation includes angularly oscillating the foot scanner until talus and navicular of the patient's foot exhibit congruency.

16. A method as recited in claim 15 wherein said angular oscillation is about an axis of rotation and said capture includes positioning the patient's foot with the center of the talus substantially aligned with the axis of rotation.

17. A method as recited in claim 16 wherein said foot measurement device includes air cushion means for capturing the patient's foot and means for deflating and inflating the air cushion, said capturing of the foot including positioning the foot on the air cushion in a deflated state and inflating said air cushion to elevate the patient's heel with the foot scanner in the first position.

18. A method as recited in claim 17 wherein said topographical record is obtained by producing a three-dimensional scan of the bottom of the patient's foot that records the distance from a reference plane to the bottom of the foot for each of an array of positions in the reference plane.

19. Apparatus for producing a custom orthotic footbed for a patient's footwear by generating a representation of the topography of the bottom of the patient's foot extending along an alignment, said apparatus comprising:
    A) means for measuring a tibial torsion angle for the patient's foot due to tibial torsion based on the orientation of the alignment axis, B) scanner means for generating the topography and having means for pivoting said scanner means about a reference position, C) means for pivoting said scanner means in a transverse plane from the reference position to a first position based upon the measured tibial torsion angle whereby the foot rests on said scanner means, D) means for capturing the foot in said scanner means at the first position relative to a reference plane, E) means for manipulating said scanner means proximate the first position until the patient's talus and navicular exhibit congruency thereby to establish a measurement position, and F) means for generating the topographical record of the foot with said scanner means in the measurement position for use in the production of the custom orthotic footbed.

20. Apparatus as recited in claim 19 wherein said tibial torsion angle measurement means includes:
i) means for positioning the patient's leg in a tibial torsion reference plane inclusive of the centers of the patient's hip, knee mass and talus, and
ii) means for measuring a tibial torsion angle as the angular transverse displacement between the tibial torsion reference plane and a tibial torsion displacement plane inclusive of the center of the talus and the interstice of the first and second toes of the patient's foot.

21. Apparatus as recited in claim 20 wherein said scanner means positioning means includes means for enabling the angular oscillation of said scanner means until talus and navicular of the patient's foot exhibit congruency.

22. Apparatus as recited in claim 21 wherein said angular oscillation enabling means defines an axis of rotation and said capture means includes means for enabling the positioning the patient's foot with the center of the talus substantially aligned with the axis of rotation.

23. Apparatus as recited in claim 22 wherein said scanner means includes air cushion means for capturing the patient's foot and means for deflating and inflating said air cushion means, whereby the foot is positioned on the air cushion in a deflated state and said means for deflating and inflating inflates said air cushion means to elevate the patient's heel above the reference plane with said scanner means is in the first position.

24. Apparatus as recited in claim 23 wherein said angular oscillation enabling means defines an axis of rotation and said capture means includes means for enabling the positioning the patient's foot with the center of the talus substantially aligned with the axis of rotation.

25. Apparatus as recited in claim 24 wherein said topographical record generating means includes three-dimensional scanner means located below the reference plane thereby to scan the bottom of the patient's foot for each of an array of positions in the reference plane.

26. Foot scanning apparatus for obtaining a representation of the bottom of a patient's foot for use in the production of a custom orthotic footbed for a foot comprising:

A) foot measurement means for generating the topography of the bottom of the foot, B) framework means for positioning said foot scanning apparatus on a support surface, and C) means for pivotally mounting said foot measurement means on said framework means whereby said foot measurement means is enabled to pivot through a limited angular range with respect to a reference position said pivotal mounting means including:

i) plate means for supporting said foot measurement means,
ii) pivot means attached to said framework means and said plate means,
iii) handle means attached to said plate means for enabling the manual pivoting of said pivotal mounting means, and
iv) indicia means on said pivotal mounting means and said framework means for indicating the angular position of said foot measurement means relative to said framework means.

27. Foot scanning apparatus as recited in claim 26 wherein:
i) said framework means includes a base plate and said pivotal mounting means includes:
ii) said plate means includes an upper plate for supporting said foot measurement means,
a lower plate spaced from said upper plate and,
support means for interconnecting said upper and lower plates,
iii) said pivot means is attached to said base plate and said lower plate, said
handle means being attached to said upper plate for enabling the manual pivoting of said pivotal mounting means, and
iv) said inidica means being on said upper plate and said framework means for indicating the angular position of said foot measurement means relative to said framework means.

28. Foot scanning apparatus as recited in claim 27 wherein said foot measurement means comprises an electrically driven scanner on said lower plate and an air cushion having a membrane on said upper plate.

29. Foot scanning apparatus as recited in claim 28 including means for inflating said air cushion and means for deflating said air cushion and means mounted on said framework means for controlling the operation of said inflating and deflating means.

30. Foot scanning apparatus as recited in claim 29 wherein said inflating and deflating means comprises an electric air pump and an electric relief valve, respectively, and wherein said controlling means includes switching means for controlling the energization of said air pump and said relief valve.

31. Foot scanning apparatus as recited in claim 28 wherein said foot scanning apparatus is located an examination station and wherein each of the patient's feet is characterized by a forefoot, a midfoot and a rear foot, said air cushion comprising:
i) reference means for defining a reference plane,
ii) foot capture means for capturing a patient's foot in a semi-weight-bearing referenced neutral position with the forefoot supported on the reference plane and the rear foot floating, said scanner obtaining an array of measurements representing the distances between the reference plane and an array of positions on the bottom of at least the rear foot, and
iii) storage means for storing the measurements from said scanner for use in the construction of the orthotic block.

32. Foot scanning apparatus as recited in claim 31 wherein said air cushion means includes means for elevating the heel above the reference plane.

33. Foot scanning apparatus as recited in claim 32 wherein said air cushion includes a flexible membrane overlying portions of said reference means.

34. Apparatus as recited in claim 31 wherein said air cushion comprises a variable volume chamber including a flexible membrane, s air pump for inflating for pressurizing said variable volume chamber whereby said membrane moves into contact with the plantar surface to contain and to support the plantar fasciae and foot structure of the patient's foot on the air cushion.

35. Foot scanning apparatus as recited in claim 34 wherein said air cushion includes support means for defining said flexible membrane with a forefoot portion at the reference plane, a rear foot portion elevated above the reference plane and an intermediate sloped portion between said forefoot and rear foot portions.

36. Apparatus as recited in claim 35 wherein the patient's foot is placed on the top of said flexible membrane and wherein said reference means includes a transparent plate on the opposite side of said flexible membrane positioned whereby at least the patient's rear foot is coextensive therewith and means for supporting said transparent plate, said scanning means including three-dimensional laser scanning means for directing a scanned laser beam through said transparent plate onto the opposite side of said flexible membrane.

* * * * *